(12) United States Patent
Lewis et al.

(10) Patent No.: US 6,716,414 B2
(45) Date of Patent: Apr. 6, 2004

(54) STABLE PHARMACEUTICAL SOLUTION FORMULATIONS FOR PRESSURIZED METERED DOSE INHALERS

(75) Inventors: David Lewis, Parma (IT); David Ganderton, Devon (GB); Brian Meakin, Batty (GB); Gaetano Brambilla, Parma (IT); Alessandra Ferraris, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 09/860,689

(22) Filed: May 21, 2001

(65) Prior Publication Data

US 2002/0025299 A1 Feb. 28, 2002

(30) Foreign Application Priority Data

May 22, 2000 (WO) ................ PCT/EP00/04635

(51) Int. Cl.$^7$ ................ A61K 9/12; A61K 9/72
(52) U.S. Cl. ................ 424/45; 424/46; 514/630; 128/200.14
(58) Field of Search ................ 424/45, 46; 514/630; 128/200.14

(56) References Cited

U.S. PATENT DOCUMENTS

| | | |
|---|---|---|
| 4,499,108 A | 2/1985 | Sequeira et al. |
| 5,955,058 A | 9/1999 | Jager et al. |
| 6,131,566 A | 10/2000 | Ashurst et al. |
| 6,150,418 A | 11/2000 | Hochrainer et al. |
| 6,290,930 B1 | 9/2001 | Blondino et al. |
| 6,315,985 B1 | 11/2001 | Wu et al. |

FOREIGN PATENT DOCUMENTS

| | | |
|---|---|---|
| EP | 0 372 777 A2 * | 6/1990 |
| WO | WO 94/13262 | 6/1994 |
| WO | WO 96/32099 | 10/1996 |
| WO | WO 99/65460 | 12/1999 |
| WO | WO 99/65464 | 12/1999 |
| WO | WO 00/23065 | 4/2000 |
| WO | WO 00/30608 | 6/2000 |

* cited by examiner

Primary Examiner—Michael G. Hartley
Assistant Examiner—Mina Haghighatian
(74) Attorney, Agent, or Firm—Oblon, Spivak, McClelland, Maier & Neustadt, P.C.

(57) ABSTRACT

An aerosol solution composition for use in an aerosol inhaler comprises an active material, a propellant containing a hydrofluoroalkane, a cosolvent and optionally a low volatility component to increase the mass median aerodynamic diameter (MMAD) of the aerosol particles on actuation of the inhaler. The composition is stabilized by using a small amount of mineral acid and a suitable can having part or all of its internal metallic surfaces made of stainless steel, anodized aluminium or lined with an inert organic coating.

25 Claims, 2 Drawing Sheets

Effect of hydrochloric acid on Acidity Function (pH')of Formoterol Fumarate Solution (12μg/100μl) in Vertrel XF/HFA containing 20% w/w Ethanol.

Effect of hydrochloric acid on Acidity Function (pH')of Formoterol Fumarate Solution (12μg/100μl) in Vertrel XF/HFA containing 20% w/w Ethanol.

Effect of hydrochloric Acid on Acidity Function (pH') of Formoterol Fumarate Solution (12μg/100μl) in Vertrel XF/HFA containing 12% w/w Ethanol (IPM = Isopropyl Myristate)

STABLE PHARMACEUTICAL SOLUTION FORMULATIONS FOR PRESSURIZED METERED DOSE INHALERS

The invention relates to stable pharmaceutical solution to be used with pressurised metered dose inhalers (MDIs) suitable for aerosol administration. In particular, the invention relates to solution to be used with pressurised metered dose inhalers (MDIs), suitable for aerosol administration containing $\beta_2$-agonists and stable at room temperature for a pharmaceutically acceptable shelf-life.

Pressurised metered dose inhalers are well known devices for administering pharmaceutical products to the respiratory tract by inhalation.

Drugs commonly delivered by inhalation include bronchodilators such as $\beta_2$-agonists and anticholinergics, corticosteroids, anti-leukotrienes, anti-allergics and other materials that may be efficiently administered by inhalation, thus increasing the therapeutic index and reducing side effects of the active material.

MDI uses a propellant to expel droplets containing the pharmaceutical product to the respiratory tract as an aerosol. Formulations for aerosol administration via MDIs can be solutions or suspensions. Solution formulations offer the advantage of being homogeneous with the active ingredient and excipients completely dissolved in the propellant vehicle or its mixture with suitable co-solvents such as ethanol. Solution formulations also obviate physical stability problems associated with suspension formulations so assuring more consistent uniform dosage administration.

For many years the preferred propellants used in aerosols for pharmaceutical use have been a group of chlorofluorocarbons which are commonly called Freons or CFCs, such as $CCl_3F$ (Freon 11 or CFC-11), $CCl_2F_2$ (Freon 12 or CFC-12), and $CClF_2$—$CClF_2$ (Freon 114 or CFC-114).

Recently, the chlorofluorocarbon (CFC) propellants such as Freon 11 and Freon 12 have been implicated in the destruction of the ozone layer and their production is being phased out.

Hydrofluoroalkanes [(HFAs) known also as hydrofluoro-carbons (HFCs)] contain no chlorine and are considered less destructive to ozone and these are proposed as substitutes for CFCs.

HFAs and in particular 1,1,1,2-tetrafluoroethane (HFA 134a) and 1,1,1,2,3,3,3-heptafluoropropane (HFA 227) have been acknowledged to be the best candidates for non-CFC propellants and a number of medicinal aerosol formulations using such HFA propellant systems have been disclosed.

Due to the higher polarity of the HFA propellants, in particular of HFA 134a (dielectric constant $D \geq 9.5$), with respect to CFC vehicles ($D \leq 2.3$), HFA solution formulations may suffer to a greater extent of chemical stability problems with respect to the corresponding CFC formulations.

Preparation of stable HFA solution formulations is even more critical when bronchodilator $\beta_2$-agonists belonging to the class of the phenylalkylamino derivatives are concerned; said drugs, like formoterol, 8-hydroxy-5-[(1R)-1-hydroxy-2-[[(1R)-2-(4-methoxyphenyl)-1-methylethyl] amino] ethyl]-2(1H)-quinolinone (hereinafter referred as TA 2005), and salbutamol (albuterol) and others, may suffer of inherent chemical stability problems due to their susceptibility to oxidative conditions; moreover, in the view of the presence of some functional groups like formamide, a higher polarity of the vehicle may accelerate the rate of solvolysis reactions.

As far as formoterol, the currently marketed CFC solutionformulation (Foradil®) exhibits a limited shelf life, i.e. 12 months at refrigerator temperature, 4±2° C., and only 3 month at room temperature.

As far as salbutamol, no formulation as HFA solution for aerosol administration currently on the market.

In the case of TA 2005, no formulation at all is currently available for aerosol administration.

In consideration of the problems outlined, it would be highly advantageous to provide a formulation in the form of HFA solution to be administered by MDI's aimed at providing pharmaceutical doses of $\beta_2$-agonists characterised by adequate shelf-life.

OBJECT OF THE INVENTION

Figure 1:
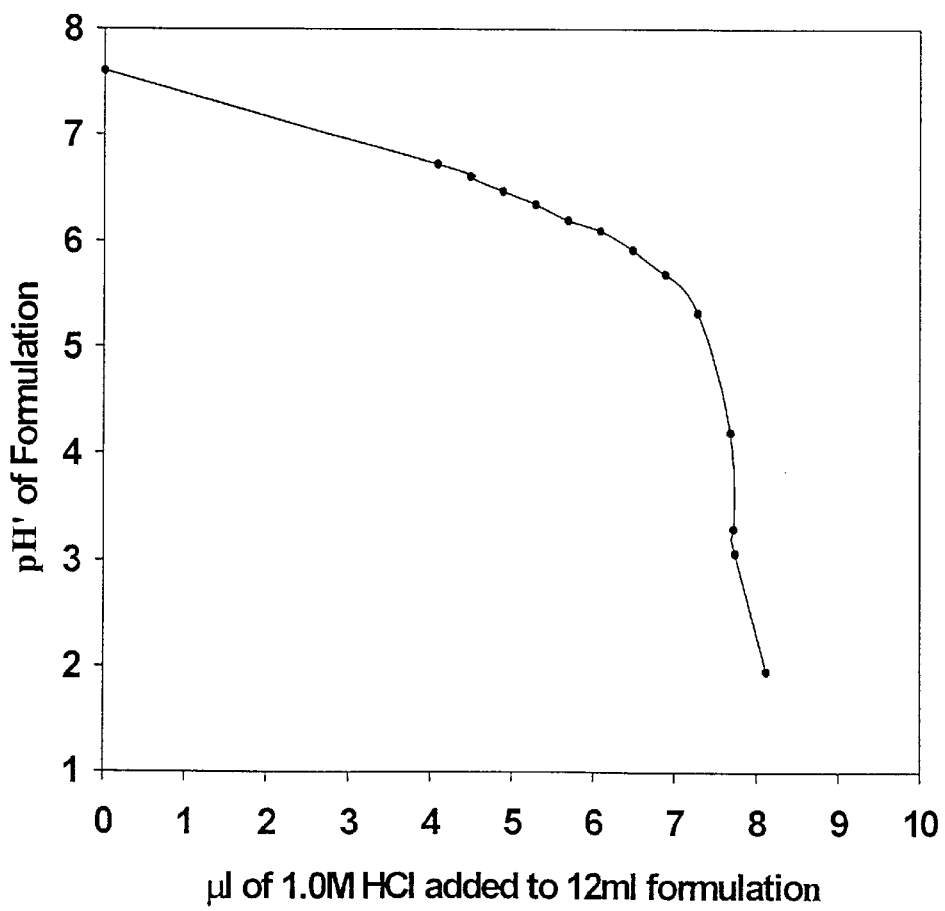
FIG. 1 shows the effect of hydrochloric acid on Acidity Function (pH') of Formoterol Fumarate Solution (12 µg/100 µL) in Vertrel XF/HFA containing 20% w/w Ethanol.

It is an object of the invention to provide a formulation in the form of HFA solution to be administered by MDI's for providing pharmaceutical doses of $\beta_2$-agonists into the low respiratory tract of patients suffering of pulmonary diseases such as asthma, characterised by adequate shelf-life. In particular, it is an object of the invention to provide a formulation in the form of HFA solution to be administered by MDI's for providing pharmaceutical doses of formoterol with a greater shelf-life of that of the formulation currently on the market.

According to the invention there is provided a pharmaceutical composition comprising a $\beta_2$-agonist belonging to the class of phenylalkylamino derivatives in a solution of a liquefied HFA propellant, a co-solvent selected from pharmaceutically acceptable alcohols, solution whose apparent pH has been adjusted to between 2.5 and 5.0 by addition of small amounts of a mineral acid. The composition of the invention shall be contained in a pressurised MDI having part or all of its internal metallic surfaces made of stainless steel, anodised aluminium or lined with an inert organic coating.

In fact, it has been found that, in the case of certain active ingredients such as $\beta_2$-agonists, their chemical stability in HFA solution formulations could be dramatically improved by a proper and combined selection of the kind of cans as well as the apparent pH range. The attribution 'apparent' is used as pH is indeed characteristic of aqueous liquids where water is the dominant component (Mole Fraction>0.95). In relatively aprotic solvents such as the HFA-ethanol vehicles used in these studies, protons are non-hydrated; their activity coefficients differ significantly from those in aqueous solution. Although the Nernst equation with respect to EMF applies and the pH-meter glass electrode system will generate a variable milli-volt output according to proton concentration and vehicle polarity, the "pH" meter reading is not a true pH value. The meter reading represents an apparent pH or acidity function (pH').

When formoterol fumarate was titrated with a strong acid in a model vehicle system commercially available (HFA 43-10MEE, Vertrel XF, Dupont), according to a method developed by the applicant, the pH' profile exhibits a shallow negative to about pH'=5.5; thereafter the acidity function drops abruptly. Surprisingly the corresponding HFA formulations turned out to much more stable below pH' 5.5. As far as TA 2005 is concerned, the pH' profile exhibits a shallow negative to about pH'=5.0; thereafter the acidity function drops quite abruptly.

On the other hand, the use of inert containers allows to avoid the leaching of metal ions or alkali as a consequence of the action of the acid contained in the formulation onto the inner walls of the cans. Metal ions such $Al^{3+}$ or alkali respectively deriving from the conventional aluminium or glass cans could in turn catalyse radical oxidative or other chemical reactions of the active ingredient which give rise to the formation of degradation products.

According to an embodiment of the invention there is also provided a pharmaceutical composition further containing a low volatility component in such a way as to, besides increasing the mass median aerodynamic diameter (MMAD) of the aerosol particles on actuation of the inhaler as explained in the following, further improving the stability of the formulation. In fact, the addition of a low volatility component with a reduced polarity with respect to the co-solvent such as an ester may allow either to reduce the amount of acid to be added for adjusting the pH and diminish the polarity of the medium so limiting the possible uptake of environmental water. In the case of active ingredients such as formoterol, it is well known that the latter (e.g. humidity) could be detrimental to the stability of the active ingredient during storage. According to a particular embodiment of the invention, there is provided a pressurised MDI for administering pharmaceutical doses consisting of an anodised aluminium container filled with a pharmaceutical composition consisting of a solution of formoterol fumarate in HFA 134a as a propellant in turn containing 12% w/w ethanol as a co-solvent and optionally isopropyl myristate as a low volatility component in an amount less/equal than 1.0% w/w, the apparent pH of said solution having been adjusted to between 3.0 and 3.5 by addition of small amounts of hydrochloric acid. The expression '% w/w' means the weight percentage of the component in respect to the total weight of the composition.

The shelf-life of the formulation put in the device of the invention could be predicted to be greater than two years at the refrigerator temperature (4–10° C.) and three months at room temperature.

According to another particular embodiment of the invention, there is provided a pressurised MDI consisting of a coated container filled with a pharmaceutical composition consisting of a solution of a combination of formoterol fumarate and beclometasone dipropionate (hereinafter BDP) in HFA 134a as a propellant in turn containing 12% w/w ethanol as a co-solvent with or without isopropyl myristate as low volatility component, the apparent pH of said solution having been adjusted to between 3.0 and 3.5 by addition of small amounts of hydrochloric acid.

According to a further particular embodiment of the invention, there is provided a pressurised MDI consisting of a coated container filled with a pharmaceutical composition consisting of a solution of TA 2005 in HFA 134a as a propellant in turn containing 12% w/w ethanol as a co-solvent with or without ispropyl myristate as a low volatility component, the apparent pH of said solution having been adjusted to between 3.0 and 5.0 by addition of small amounts of hydrochloric acid.

However, a person sufficiently skilled in the art can easily apply the teaching of the present invention to the preparation of HFA solution formulations containing other active ingredients bearing functional groupssensitive to hydrolytic and/or oxidative reactions, such as formamide and cathecol respectively.

WO 97/47286, EP 513127, EP 504112, WO 93/11747, WO 94/21228, WO 94/21229, WO 96/18384, WO 96/19198, WO 96/19968, WO 98/05302, WO 98/34595 and WO 00/07567 disclose HFA formulations in the form of suspensions in which $\beta_2$-agonists such formoterol and salbutamol are either exemplified and/or claimed.

WO 99/65464 refers to HFA formulations containg two or more active ingredients in which at least one is in suspension. The preferred formulations comprises salbutamol sulphate in suspension.

In WO 98/34596, the applicant described solution compositions for use in an aerosol inhaler, comprising an active material, a propellant containing a hydrofluoroalkane (HFA), a cosolvent and further comprising a low volatility component to increase the mass median aerodynamic diameter (MMAD) of the aerosol particles on actuation of the inhaler. Said application does not address the technical problem of the chemical stability of the active ingredient but it rather concern the drug delivery to lungs.

In the international application no PCT/EP99/09002 filed on Nov. 23, 1999 published on Jun. 2, 2000 as WO 00/30608 the applicant has disclosed pressurised MDI's for dispensing solution of an active ingredient in a hydrofluorocarbon propellant, a co-solvent and optionally a low-volatility component characterized in that part or all of the internal surfaces of said inhalers consist of stainless steel, anodised aluminium or are lined with an inert organic coating. The examples are referred only to steroids and anticholinergic agents. As demonstrated in the example 1 of the present application, the use of coated containers, even in the presence of an organic acid, is not sufficient for providing stable solution formulations of a phenylalkylamino derivative such as salbutamol.

EP 673240 proposes the use of acids as stabilisers preventing the chemical degradation of the active ingredient in aerosol solution formulations comprising HFAs. Most examples relate to ipratropium bromide, an anticholinergic drug and only an example is presented for a $\beta_2$-agonist, i.e. fenoterol. Although salbutamol is claimed, no exemplary formulations are provided. Moreover, the stability data are reported only for ipratropium and the patentee does not either make difference between the use of organic and inorganic acids. It is indeed evident from the data reported in the example 1 of the present application, that salbutamol cannot be stabilised at all by addition of organic acids even when stored in coated cans. Furthermore, apart from ipratropium bromide, in EP 673240 no guidance is given with respect to the amount of acid which has to be added in order to stabilise the medicaments without compromising the stability of the whole composition in the can. The only hint can be found on page 5, lines 15 to 16 which says that an amount of inorganic acid should be added to obtain a pH value from 1 to 7, so a very broad and generic range.

WO 98/34596 refers to solution formulations containing a propellant and a physiologically acceptable polymer which could help the solubilisation and the stability as well of the active ingredients.

WO 00/06121 refers to propellant mixtures for aerosol dinitrogen monoxide and a hydrofluoroalkane in the preparation of suspension and solution aerosols. The use of dinitrogen monoxide may improve the stability at storage of oxidation-sensitive active ingredients. As far as $\beta_2$-agonist such as levosalbutamol sulphate, formoterol fumarate and salmeterol xinafoate, only examples referred to suspensions are reported.

WO 99/65460 claims pressurised MDI's containing stable formulations of a β-agonist drug in suspension or solution.

Examples refer to solutions of formoterol fumarate containing an HFA propellant and ethanol as co-solvent, filled in conventional aluminium or plastic coated glass cans.

Samples stored under accelerated conditions (40° C., 75% relative humidity) for a very short period, one month, exhibited about 10% loss of drug. According to pharmaceutical guidelines on stability, loss of 10% of active ingredient does not meet the criteria of acceptance. Moreover, as it is evident from the data reported in Example 2 of the present application, following the teaching of WO 99/65460 stable formoterol solution formulations cannot be provided. The applicant has indeed demonstrated that the presence of low-volatility components does not substantially affect the chemical stability of the compositions. In some cases, they could even improve it.

According to a further aspect of the invention there is provided a method of filling an aerosol inhaler with a composition of the invention, the method comprising:

(a) Preparation of a solution of one or more active ingredients in one or more co-solvents optionally containing an appropriate amount of a low volatility component (b) Filling of the device with said solution (c) Adding a pre-determined amount of a strong mineral acid (d) Adding a propellant containing a hydrofluoroalkane (HFA)

(e) Crimping with valves and gassing

Active ingredients which may be used in the aerosol compositions of the invention are short- and long-acting $\beta_2$-adrenergic agonists such as salbutamol, formoterol, salmeterol, TA 2005 andsalt thereof and their combinations with steroids such as beclomethasone dipropionate, fluticasone propionate, budesonide and its 22R-epimer or with anticholinergic atropine-like derivatives such as ipratropium bromide, oxitropium bromide, tiotropium bromide.

Preferably the active ingredient is a long acting $\beta_2$-agonists belonging to the formula sketched below

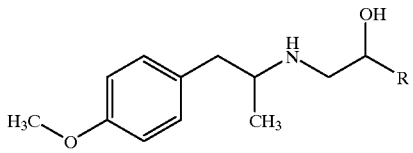

wherein R is more preferably 1-formylamino-2-hydroxyphen-5-yl (formoterol) or 8-hydroxy-2(1H)-quinolinon-5-yl (TA 2005) or one of their corresponding stereoisomers. Other amino type drugs bearing functional groups sensitive to oxidative and/or hydrolytic reactions can be advantageously used. Although the preferred formulations of the invention are in the form of solutions, in case of the combinations, one of the two active ingredients could be present in suspension.

We prefer the formulation to be suitable for delivering a therapeutic amount of the active ingredient in one or two actuations. Preferably the formulation will be suitable for delivering 6–12 µg/dose of formoterol fumarate either alone or in combination. In the case of TA 2005, the formulation will be advantageously suitable for delivering 2–10 µg/dose, preferably 3–5 µg/dose. For "dose" we mean the amount of active ingredient delivered by a single actuation of the inhaler.

The formulations of the invention will be contained in cans having part of all of the internal surfaces made of anodised aluminium, stainless steel or lined with an inert organic coating. Examples of preferred coatings are epoxyphenol resins, perfluoroalkoxyalkane, perfluoroalkoxyalkylene, perfluoroalkylenes such as polytetrafluoroethylene, fluorinated-ethylene-propylene, polyether sulfone and a copolymer fluorinated-ethylene-propylene polyether sulfone. Other suitable coatings could be polyamide, polyimide, polyamideimide, polyphenylene sulfide or their combinations.

To further improve the stability, cans having a rolled-in rim and preferably a part or full rollover rim are used.

The formulation is actuated by a metering valve capable of delivering a volume of between 50 µl and 100 µl.

Metering valves fitted with gaskets made of chloroprene-based rubbers can preferably be used to reduce the ingress of moisture which, as previously mentioned, can adversely affect the stability of the drug during storage. Optionally, further protection can be achieved by packaging the product in a sealed aluminium pouch.

The hydrofluorocarbon propellant is preferably selected from the group of HFA 134a, HFA 227 and mixtures thereof.

The co-solvent is usually an alcohol, preferably ethanol.

The low volatility component, when present, has a vapour pressure at 25° C. lower than 0.1 kPa, preferably lower than 0.05 kPa. Advantageously, it could be selected from the group of glycols, particularly propylene glycol, polyethylene glycol and glycerol or esters, for example ascorbyl palmitate, isopropyl myristate and tocopherol esters.

The compositions of the invention may contain from 0.1 to 10% w/w of said low volatility component, preferably between 0.3 to 5% w/w, more preferably between 0.4 and 2.0% w/w.

Propylene glycol, polyethylene glycol, glycerol with residual water less than 0.1% w/w and esters of long-chain fatty acids are the preferred low-volatility components. More preferred are those with a dipole moment less than 2.0 or with a dielectric static constant less than 20, preferably less than 10. Particularly preferred is isopropyl myristate.

The function of the low volatility component is to modulate the MMAD of the aerosol particles and optionally to further improve the stability of the formulation. With respect to the latter aspect, particularly preferred is the use of isopropyl myristate.

The apparent pH range is advantageously comprised between 2.5 and 5.0, preferably between 3.0 and 4.5, even more preferably between 3.0 and 3.5. Strong mineral acids such as hydrochloric, nitric, phosphoric are preferably used to adjust the apparent pH.

The amount of acid to be added to reach the desired apparent pH will be pre-determined in the model vehicle reported before and it will depend on the type and concentration of the active ingredient. In the case of the preferred formulations of formoterol fumarate and its combination with beclometasone dipropionate, an amount comprised between 3 and 3.5 µl of 1.0 M hydrochloric acid should be added.

The following examples further illustrate the invention.

EXAMPLE 1

Stability of Salbutamol (100 µg/dose)-HFA 134a Solution as Such and in the Presence of Different Organic Acids.

Compositions containing 24 mg of salbutamol (100 µg/dose), 10–20% (w/w) ethanol in HFA 134a put in 12 mL epoxy phenol resin lacquered cans, with or without addition of different organic acids, were stored at 40–50° C.

The results in term of stability expressed as percentage of remaining drug determined by HPLC, are reported in Table

1.

TABLE 1

| | % SALBUTAMOL | |
|---|---|---|
| Acid | t = 42 days | t = 1.5 months at 4° C. |
| None | 69% | — |
| Oleic | 69–70% | — |
| Xinafoic | 70% | — |
| Citric (0.41 w/w) | — | 40.0 |
| Citric (0.02 w/w) | — | 55.1 |
| 30% Acetic acid (0.4% w/w) | — | 49.6 |
| 30% Acetic acid (0.14% w/w) | — | 73.8 |

The results show that the addition of organic acids does not improve the stability of salbutamol even when coated cans are used.

EXAMPLE 2

Stability of Formoterol (12 μg/100 μl)-HFA 134a Compositions in Epoxy-phenol Resin Lacquered Cans.

Solution formulations were prepared by dissolving 1.44 mg of formoterol fumarate in HFA 134a in turn containing 15% w/w ethanol and 1.3% w/w glycerol. pMDIs were stored upright over the range 4–50° C. for up to 28 days. Formoterol content was determined by HPLC and the percent residual concentrations calculated relative to the 12 μg/shot nominal dose. The percent residual formoterol concentration is reported in Table 2. Derived Arrhenius parameters were used to estimate rate constants at ambient temperature (18–25°) and solutions stored in a domestic refrigerator (4–10°); these rate constants were used to calculate predicted shelf-life for 5% and 10% degradation of formoterol (Table 3).

The calculated shelf-life data in Table 3 indicates that formoterol is not stable in this HFA 134a-ethanol-glycerol vehicle.

TABLE 2

Degradation Rate Data for Formoterol-HFA 134a
pMDI Solutions (12 μg/100 μl)
Vehicle: HFA 134a with 1.3% w/w Glycerol, 15.0% w/w Ethanol
Epoxy-phenol lacquered cans stored upright

| | Percent Residual Conc. Formoterol | | | | |
|---|---|---|---|---|---|
| Time (days) | 50° C. | 43° C. | 40° C. | 25° C. | 4° C. |
| Initial | 99.7 | 99.7 | 99.7 | 99.7 | 99.7 |
| 2 | 92.5 | — | — | — | — |
| 4 | 87.2 | 89.4 | — | — | — |
| 6 | 80.6 | — | — | — | — |
| 7 | — | — | 89.0 | — | — |
| 10 | 74.9 | — | — | — | — |
| 12 | 72.1 | 79.4 | — | — | — |
| 14 | 67.0 | — | 81.7 | 92.0 | — |
| 16 | 64.4 | 75.7 | — | — | — |
| 18 | 59.5 | — | — | — | — |
| 20 | 59.5 | 74.5 | — | — | — |
| 24 | 54.6 | 68.6 | — | — | — |
| 28 | 47.2 | 63.3 | 71.3 | 86.6 | 96.7 |
| r | 0.995 | 0.989 | 0.993 | 0.997 | — |
| Rate Constant (day$^{-1}$ x 10$^2$) | 2.53 | 1.49 | 1.17 | 0.51 | 0.11 |

Arrhenius Plot Parameters: K = Ae$^{E/RT}$
A = 2.28 x 10$^6$ day$^{-1}$; E = 49.4 kJ mol$^{-1}$; r = 0.9985

TABLE 3

Predicted Shelf Life Data for Formoterol-HFA 134a pMDI
Solutions (12 μg/100 μl)
Vehicle: HFA 134a with 1.3% w/w Glycerol, 15% w/w Ethanol
Epoxy-phenol lacquered cans stored upright

| | Rate Constant | Shelf-Life (days) | |
|---|---|---|---|
| Temperature | (day$^{-1}$ x 10$^3$) | $t_{10\%}$ | $t_{5\%}$ |
| 4° C. | 1.10 | 95 | 47 |
| 10° C. | 1.74 | 60 | 29 |
| 20° C. | 3.51 | 30 | 15 |
| 25° C. | 4.93 | 21 | 10 |

EXAMPLE 3

Effect of Hydrochloric Acid on Solution pH' (Acidity Function)

(a) 1.0 M hydrochloric acid was added incrementally to 50 mL of HFA 43-10MEE (Vertrel XF) containing 20% w/w ethanol and pH' measured after each aliquot of acid. FIG. 1 shows the resultant titration curve normalised to the usual fill volume of a pMDI can (12 L). The pH' profile exhibits a shallow negative slope to about pH'=5.5; thereafter the acidity function drops abruptly.

Figure 2:
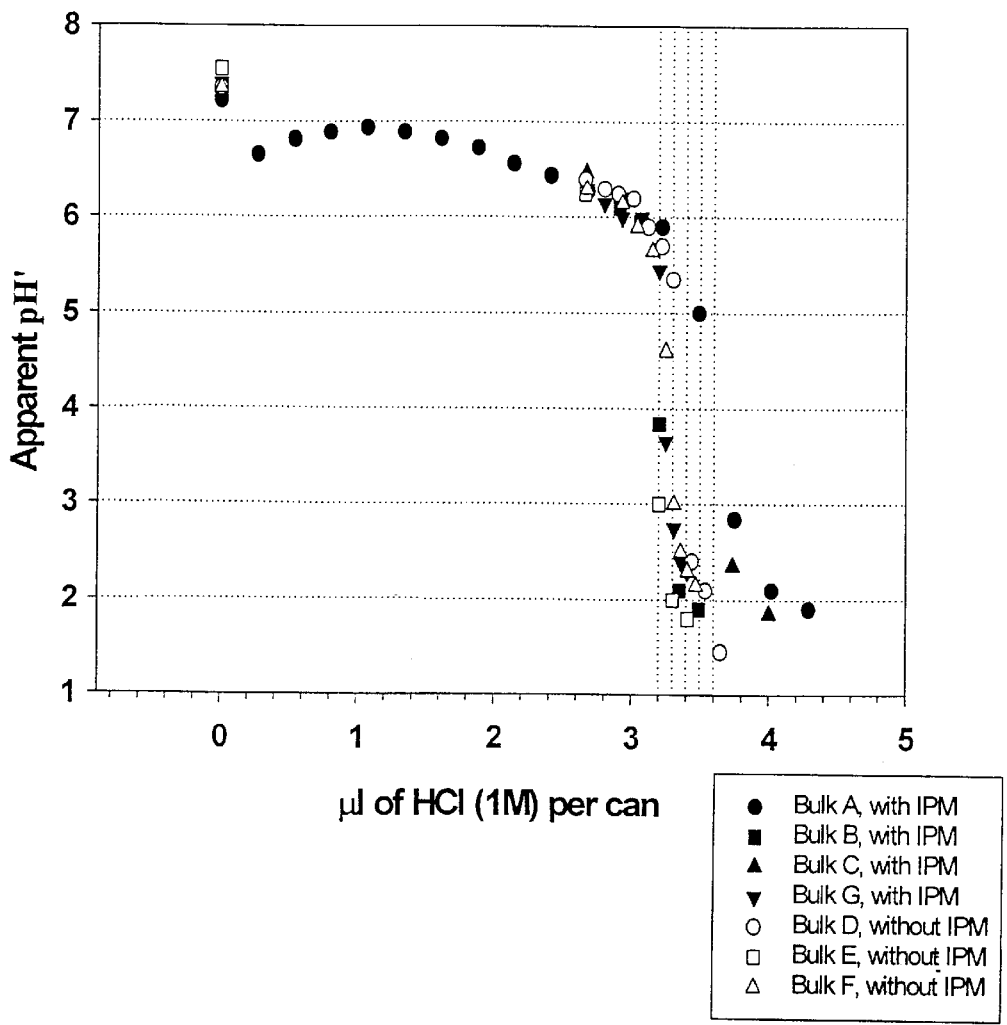
FIG. 2 shows the effect of hydrochloric Acid on Acidity Function (pH') of Formoterol Fumarate Solution (12 µg/100 µL) in Vertrel XF/HFA containing 12% w/w Ethanol.

(b) Experiment (a) was repeated with formoterol formulations containing a lower concentration of ethanol (12% w/w) and with the addition of 1.0% isopropyl myristate. The resultant pH profile, shown in FIG. 2 is similar in shape with the abrupt fall in pH' per unit increment of acid again commencing at about pH'=5.5. However, only about half the acid is required to achieve the same reduction in pH'. This is largely due to the reduction in ethanol content; FIG. 2 also shows similarity in the profiles obtained with and without isopropyl myristate.

EXAMPLE 4

Effect of pH' on Stability of Formoterol Solutions in HFA 43-10MEE Containing 20% w/w Ethanol Aliquots of 1.0 M hydrochloric acid were added to 12 mL of formoterol solution in glass vials. After measurement of pH, valves were crimped on and the vials stored upright at 50° C.: Vial samples containing different concentrations of acid were assayed for residual formoterol after 10 and 20 days storage. The pH' of a third vial was determined after 40 days storage. Results are shown in Table 4. Table 4 shows changes in pH on storage; this is probably largely associated with leaching of alkali from the soft glass of the vials. However, overall consideration of the pH' and formoterol content data implies that the stability of a solution formulation of the drug in HFA can be improved by the addition of mineral acid to provide a formulation with pH' between 2.5–5.0.

TABLE 4 pH' and Formoterol Content of Formoterol-Vertrel XF/HFA
Solutions (12 μg/100 μl)
Vehicle: Vertrel XF/HFA with 20% Ethanol and Hydrochloric
Acid
St Gobain glass vials stored upright

| Acidity Function (pH') | | Percent Residual Conc. Formoterol | | |
|---|---|---|---|---|
| Initial | 40 days | Initial | 10 days | 20 days |
| 1.8 | 2.8 | 100 | 4.8 | Nil |
| 2.1 | 4.4 | 100 | 75.1 | 70.7 |

TABLE 4-continued pH' and Formoterol Content of Formoterol-Vertrel XF/HFA
Solutions (12 μg/100 μl)
Vehicle: Vertrel XF/HFA with 20% Ethanol and Hydrochloric
Acid
St Gobain glass vials stored upright

| Acidity Function (pH') | | Percent Residual Conc. Formoterol | | |
|---|---|---|---|---|
| Initial | 40 days | Initial | 10 days | 20 days |
| 2.6 | 4.2 | 100 | 97.2 | 86.7 |
| 3.3 | 4.2 | 100 | 97.1 | 89.9 |
| 5.6 | 6.6 | 100 | 95.8 | 92.1 |
| 7.4 | 6.7 | 100 | 85.4 | 67.2 |

EXAMPLE 5

Stability of Acidified Formoterol-HFA 134a Solutions in Anodised Cans

Formoterol formulations (12 μg/100 μl) were prepared by dissolving 1.44 mg of formoterol fumarate in HFA 134a containing 12% w/w ethanol with and without 1.0% w/w isopropyl myristate. The latter was included as a non-volatile excipient with the potential for increasing MMAD if so desired. It also improves the solubility of formoterol in the vehicle and reduces polarity of the vehicle compared to the addition of glycerol.

pMDI cans containing 3.1–3.4 μl 1.0 M hydrochloric acid were set down on storage, upright and inverted, at 4° C. to 50° C. and samples taken for analysis of formoterol content at appropriate intervals.

Stability data obtained after 70 days of storage are given in Table 5.

A matrix of formulations containing 1.44 mg (12 μg/100 μl) formoterol fumarate were prepared in HFA 134a containing 12.0% w/w ethanol with or without 1.0% w/w isopropyl myristate as non-volatile excipient. Aliquots of drug concentrate were transferred to anodised cans and 3.15–3.35 μl of 1.0M hydrochloric acid added prior to crimping with 50 μl valves and gassing between 22 and 28 replicates at each acid strength were prepared.

To determine residual formoterol, 30×50 μl shots were discharges into DUSA tubes. The acid range selected was anticipated to give pH' values of 3.0–3.5 and to determine the formulation sensitivity to small changes in acid concentration. Cans were placed on stored upright and inverted (valve up and down respectively) at 25–50° C.

Table 5 shows the results obtained at 40° and 50° after 11–40 day's storage. Each value (expressed as percent nominal drug concentration) is obtained from a different can.

Initial values were obtained for two cans of each acid strength. Inspection of the data shows all assay values to within the reproducibility of the HPLC assay and independent of acid strength. A similar conclusion was drawn for the storage time point replicates, i.e., independent of acid strength (3.2–3.3 μl) or whether cans were stored upright or inverted. Consequently for kinetics calculation the mean value for initial (n=10) and subsequent time points (n=6) was used.

In Table 6 are reported the Arrhenius parameters together with estimated shelf lives at 4, 10 and 25° C. The $t_{5\%}$ is predicted to be greater than 3 months at ambient temperature and approximately 2 years at 4° C.

TABLE 5

Stability Data for Formoterol Fumarate Solutions (12 μg/100 μl)
in HFA 134a containing 12.0% Ethanol ± 1.0% Isopropyl Myristate
(values are expressed as percent nominal)
Anodised cans fitted with 50 μl valves/30 doses collected per can
Different cans assessed at each condition
Cans stored upright (* inverted)

| | STORAGE CONDITION/No isopropyl myristate | | | | | | | |
|---|---|---|---|---|---|---|---|---|
| 1.0M HCl | Initial | | 40° C.; 40 days | | 50° C.; 11 days | | 50° C.; 33 days | |
| μl per Can | 1st Can | 2nd Can | 1st Can | 2nd Can | 1st Can | 2nd Can | 1st Can | 2nd Can |
| 3.15 | 99.8 | 99.6 | — | — | — | — | — | — |
| 3.20 | 100.8 | 99.7 | 96.0 | 93.2* | 96.7 | 96.5 | 88.5 | 89.9* |
| 3.25 | 97.9 | 98.8 | 93.9 | 94.3* | 96.4 | 96.5 | 92.2 | 91.5* |
| 3.30 | 97.3 | 98.9 | 93.7 | 93.7* | 97.0 | 89.1 | 90.9 | 92.8* |
| 3.35 | 100.0 | 98.3 | — | — | — | — | — | — |
| Mean | 99.1 | | 94.1 | | 95.4 | | 91.0 | |
| C.V. | 1.1% | | 1.0% | | 3.2% | | 1.8% | |

| | STORAGE CONDITION/1.0% isopropyl myristate | | | | | | | |
|---|---|---|---|---|---|---|---|---|
| 1.0M Hcl | Initial | | 40° C.; 33 days | | 50° C.; 11 days | | 50° C.; 31 days | |
| μl per Can | 1st Can | 2nd Can | 1st Can | 2nd Can | 1st Can | 2nd Can | 1st Can | 2nd Can |
| 3.15 | 101.1 | 99.3 | — | — | — | — | — | — |
| 3.20 | 97.0 | 100.2 | 94.4 | 93.2* | 93.8 | 93.6 | 90.6 | 92.7* |
| 3.25 | 101.4 | 100.2 | 98.6 | 95.0* | 96.1 | 95.9 | 91.6 | 89.7* |
| 3.30 | 99.9 | 100.8 | 92.8 | 95.3* | 95.6 | 95.7 | 90.0 | 89.6* |
| 3.35 | 99.2 | 97.2 | — | — | — | — | — | — |
| Mean | 99.6 | | 94.9 | | 95.1 | | 90.7 | |
| C.V. | 1.5% | | 2.2% | | 1.2% | | 1.4% | |

TABLE 6

Shelf Life Prediction for Acidified Formoterol Fumarate Solution
(12 μg/100 μl) in HFA 134a containing
12% w/w Ethanol ± 1.0% w/w isopropyl Myristate (IPM)
Anodised aluminium cans

| | FORMOTEROL FUMARATE (percent nominal) | | | |
|---|---|---|---|---|
| TIME | | | 40° C. | |
| (days) | Nil IPM | 1% IPM | Nil IPM | 1% IPM |
| 0 | 99.1 | 99.6 | 99.1 | 99.6 |
| 11 | 95.4 | 95.1 | — | — |
| 31 | — | 90.7 | — | — |
| 33 | 91.0 | — | — | 94.9 |
| 40 | — | — | 94.1 | — |
| Rate Const. ($day^{-1} \times 10^3$) | 2.52 | 2.94 | 1.29 | 1.46 |

| Arrhenius Parameters | Frequency Factor ($day^{-1}$) | Activation Energy (kJ $mol^{-1}$) |
|---|---|---|
| Nil IPM | $3.19 \times 10^6$ | 56.3 |
| 1% w/w IPM | $9.63 \times 10^6$ | 58.9 |

| | Nil IPM | | | 1.0% w/w IPM | | |
|---|---|---|---|---|---|---|
| TEMPER-ATURE | Rate Const. ($day^{-1}$) | $t_{10\%}$ (days) | $t_{5\%}$ (days) | Rate Const. ($day^{-1}$) | $t_{10\%}$ (days) | $t_{5\%}$ (days) |
| 4° C. | $7.8 \times 10^{-5}$ | 1344 | 657 | $7.8 \times 10^{-5}$ | 1360 | 664 |
| 10° C. | $1.3 \times 10^{-4}$ | 802 | 392 | $1.3 \times 10^{-4}$ | 789 | 386 |
| 25° C. | $4.4 \times 10^{-4}$ | 240 | 117 | $4.4 \times 10^{-4}$ | 225 | 110 |

EXAMPLE 6
Stability of Acidified Formoterol/BDP-HFA 134a Solutions in Cans Coated with a Fluorocarbon Polymer (DuPont 3200-200).

Formoterol and BDP combination formulations equivalent to doses of 6 µg/50 µl and 100 µg/50 µl respectively, were prepared by dissolving 1.44 mg of formoterol fumarate and 24 mg of BDP in HFA 134a containing 12% w/w ethanol and 0.4% w/w of isopropyl myristate. pMDI coated cans containing 3.25 µl 1.0 M hydrochloric acid were set down on storage inverted, at 4° C. and samples taken for analysis of formoterol and BDP contents at appropriate intervals.

Stability data obtained are given in Table 7.

Each value is expressed as percent nominal drug concentration.

The results indicate that the formulation is stable for at least 4 months at 4° C.

EXAMPLE 7
Stability of Acidified TA 2005-HFA 134a Solutions in Cans Coated with a Fluorocarbon Polymer (DuPont 3200-200).

TA 2005 (3.5 µg/50 µl) were prepared by dissolving 0.84 mg of the active ingredient in HFA 134a containing 12% w/w ethanol and 1.0% w/w of ispropyl myristate. pMDI coated cans containing 1.0, 1.4 and 1.8 µl 0.08 M hydrochloric acid (corresponding respectively to an apparent pH of about 4.8, 3.2 and 2.9) were set down on storage, upright at 50° C., and samples taken for analysis of TA 2005 contents at appropriate intervals.

Stability data obtained are given in Table 8.

Each value is expressed as percent nominal drug concentration.

The results indicate that the formulations in which the apparent pH is comprised between 3.0 and 5.0 are stable (i.e give rise to much less than 10% loss of drug) for almost three months at 50° C., while that corresponding to an apparent pH of less than 3, not.

TABLE 7

Formoterol/BDP combination formulations of Ex 6 - Stability data at 4° C.

| | | Storage Condition | |
| --- | --- | --- | --- |
| | Initial | 4° C.; 64 days inverted | 4° C.; 123 days inverted |
| Formoterol | 104.7 | 95.10 | 99.9 |
| BDP | 99.4 | 100.10 | 102.6 |

TABLE 8

TA 2005 formulations of Ex 7 - Stability data at 50° C.

| | | Storage Condition | |
| --- | --- | --- | --- |
| 0.08M HCl µl per can | Initial | 50° C.; 22 days upright | 50° C.; 83 days upright |
| 1.0 | 100.0 | 98.3 | 99.4 |
| 1.4 | 100.0 | 98.2 | 98.8 |
| 1.8 | 100.0 | 90.2 | 88.1 |

What is claimed is:

1. A composition, comprising:
   formoterol, a stereoisomer of formoterol, or a salt of formoterol, in a solution of a:
   liquefied HFA propellant,
   a co-solvent selected from pharmaceutically acceptable alcohols, and
   a mineral acid,
   wherein said solution has a pH between about 2.5 and about 5.0.

2. The composition of claim 1, comprising formoterol, a stereoisomer of formoterol or a salt of formoterol in combination with a steroid or an anticholinergic atropine-like derivative.

3. The composition of claim 2, comprising a steroid selected from the group consisting of beclomethasone dipropionate, fluticasone propionate, budesonide or its 22R-epimer.

4. The composition of claim 2, comprising an anticholinergic atropine-like derivative selected from the group consisting of ipratropium bromide, oxitropium bromide or tiotropium bromide.

5. The composition of claim 2, wherein at least one of formoterol, a stereoisomer of formoterol, or a salt of formoterol, is in suspension.

6. The composition of claim 1, wherein said mineral acid comprises hydrochloric acid, nitric add or phosphoric acid.

7. A container comprising the composition of claim 1, wherein said container has part or all of its internal metallic surfaces made of stainless steel, anodised aluminum or is lined with an inert organic coating.

8. The container of claim 7, which is lined with an inert organic coating selected from the group consisting of one or more epoxy-phenol resins, perfluoroalkoxyalkane, perfluoroalkoxyalkylene, perfluoroalkylenes, polytetrafluoroethylene, fluorinated-ethylene-propylene, polyether sulfone and a copolymer fluorinated-ethylene-propylene polyether sulfone.

9. The container of claim 8, which is lined with polytetrafluoroethylene.

10. The composition of claim 1, which comprises formoterol fumarate and wherein the pH of said solution is between about 3.0 and about 3.5.

11. The composition of claim 1, further comprising a low volatility component with a vapor pressure at 25° C. of not more tan 0.1 kPa.

12. The composition of claim 1, further comprising a low volatility component wit a vapor pressure at 25° C. of not more than 0.05 kPa.

13. A composition according to claim 11, wherein said solution includes at least 0.2% by weight and not more tan 10% by weight of said low volatility component.

14. The composition of claim 11, wherein said low volatility component is a glycol or an ester of a long-chain fatty acid.

15. The composition of claim 1, wherein said propellant comprises one or more HFAs selected from the group consisting of HFA 134a and HFA 227.

16. The composition according to claim 1, wherein said co-solvent comprises an alcohol, which is not ethanol.

17. The composition according to claim 1, wherein said co-solvent comprises ethanol.

18. A method for preparing an aerosol composition which comprises formoterol, a stereoisomer of formoterol, or a salt of formoterol, in a solution of a liquefied HPA propellant, a co-solvent and a mineral acid, said method comprising:

(a) preparing a solution of one or more of formoterol, a stereoisomer of formoterol, or a salt of formoterol, in one or more cosolvent(s) optionally containing an appropriate amount of a low volatility component;

(a) filling a device with said solution;

(c) adding a mineral acid to said solution in such an amount to obtain a pH between about 2.5 and about 5.0;

(d) adding a propellant containing a hydrofluoro-alkane (HFA) to said solution; and (e) crimping said device with a valve and gassing.

19. The method of claim 18, wherein the composition further comprises a steroid or an anticholinergic atropine-like derivative.

20. The method of claim 19, wherein the composition comprises formoterol fumarate and wherein the pH of said solution is between about 3.0 and about 3.5.

21. An aerosol produced from the composition of claim 1.

22. A metered dose inhaler comprising the composition of claim 1.

23. A method for administering formoterol, a stereoisomer of formoterol or a salt of formoterol to a subject in need thereof, comprising producing an aerosol from the composition of claim 1 and administering said aerosol to said subject.

24. The composition on of claim 1, comprising formoterol fumarate and beclomethasone dipropionate.

25. A sealed aluminum pouch enclosing the container of claim 7.

* * * * *